United States Patent
Heumann et al.

(10) Patent No.: US 9,782,544 B2
(45) Date of Patent: Oct. 10, 2017

(54) SUPPLEMENTAL DEVICE FOR USE WITH AN INJECTION DEVICE

(71) Applicant: Sanofi-Aventis Deutschland GmbH, Frankfurt am Main (DE)

(72) Inventors: Gunter Heumann, Jena (DE); Gertrud Blei, Jena (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/784,045

(22) PCT Filed: Apr. 16, 2014

(86) PCT No.: PCT/EP2014/057781
§ 371 (c)(1),
(2) Date: Oct. 13, 2015

(87) PCT Pub. No.: WO2014/173770
PCT Pub. Date: Oct. 30, 2014

(65) Prior Publication Data
US 2016/0074593 A1    Mar. 17, 2016

(30) Foreign Application Priority Data
Apr. 22, 2013 (EP) .................................... 13164750

(51) Int. Cl.
*A61M 5/315* (2006.01)
*G01J 3/46* (2006.01)
(Continued)

(52) U.S. Cl.
CPC .......... *A61M 5/31568* (2013.01); *A61M 5/28* (2013.01); *A61M 5/31551* (2013.01);
(Continued)

(58) Field of Classification Search
None
See application file for complete search history.

(56) References Cited

U.S. PATENT DOCUMENTS

| 5,963,333 A | 10/1999 | Walowit et al. |
| 6,020,583 A * | 2/2000 | Walowit ................ G01J 3/0251 250/226 |

(Continued)

FOREIGN PATENT DOCUMENTS

| WO | 2006120182 A1 | 11/2006 |
| WO | 2011117212 A1 | 9/2011 |
| WO | 2013004843 A1 | 1/2013 |

OTHER PUBLICATIONS

Extended European Search Report issued in European Patent Application No. 13164750.5 dated Jul. 31, 2013.

*Primary Examiner* — Shawn Decenzo
(74) *Attorney, Agent, or Firm* — McDonnell Boehnen Hulbert & Berghoff LLP

(57) ABSTRACT

A supplemental device comprising: a connector configured to attach the supplemental device to an injection device in use; a sensor configured to generate sensor output dependent on an intensity of light on the sensor and having a field of view directed at a surface area of the injection device in use, the surface area being external to the supplemental device; a light source configured to generate illumination which in use can be directed out of the supplemental device onto the surface area; a shield configured to limit the field of view of the sensor such that the field of view is entirely directed at the surface area in use; and a processor configured to use the sensor output generated when illumination from the light source is reflected from the surface area to determine a property of the injection device.

18 Claims, 6 Drawing Sheets

(51) Int. Cl.
*A61M 5/28* (2006.01)
*A61M 5/31* (2006.01)

(52) U.S. Cl.
CPC . *A61M 2005/3126* (2013.01); *A61M 2205/18* (2013.01); *A61M 2205/3306* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/6081* (2013.01)

(56) References Cited

U.S. PATENT DOCUMENTS

| | | | |
|---|---|---|---|
| 6,369,895 B1* | 4/2002 | Keeney | G01J 3/50 356/402 |
| 2005/0283065 A1* | 12/2005 | Babayoff | A61B 1/00009 600/407 |
| 2011/0063615 A1* | 3/2011 | Shimbo | G01J 3/02 356/326 |
| 2011/0238017 A1* | 9/2011 | Watanabe | A61M 5/14546 604/189 |
| 2012/0092670 A1* | 4/2012 | Chatow | G01J 3/524 356/402 |
| 2013/0072897 A1 | 3/2013 | Day et al. | |

* cited by examiner

SUPPLEMENTAL DEVICE FOR USE WITH AN INJECTION DEVICE

CROSS REFERENCE TO RELATED APPLICATIONS

The present application is a U.S. National Phase Application pursuant to 35 U.S.C. §371 of International Application No. PCT/EP2014/057781 filed Apr. 16, 2014, which claims priority to European Patent Application No. 13164750.5 filed Apr. 22, 2013. The entire disclosure contents of these applications are herewith incorporated by reference into the present application.

FIELD OF INVENTION

An aspect of the present invention relates to a supplemental device for use with an injection device and relates particularly, but not exclusively, to a supplemental device for use with an injection device that is used to inject medicament such as insulin.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses that are administered. Supplemental devices may be used to record information about the various times at which insulin doses are administered and the quantity of insulin administered during each such dose.

Problems may arise however when a patient does not keep a record of what type of insulin they are using, and in more serious cases when a patient uses the wrong type of insulin. Aspects of the present invention address the foregoing.

Colour detection is disclosed in the prior art, for instance in WO2011/117212 and US2011/0238017.

SUMMARY

According to an aspect of the present invention there is provided a supplemental device comprising:

a connector configured to attach the supplemental device to an injection device in use;

a sensor configured to generate sensor output dependent on an intensity of light on the sensor and having a field of view directed at a surface area of the injection device in use, the surface area being external to the supplemental device;

a light source configured to generate illumination which in use can be directed out of the supplemental device onto the surface area;

a shield configured to limit the field of view of the sensor such that the field of view is entirely directed at the surface area in use; and a processor configured to use the sensor output generated when illumination from the light source is reflected from the surface area to determine a property of the injection device.

This improves the reliability of the supplemental device because light that has not been reflected from the surface area of the injection device, mentioned in the foregoing aspect, cannot influence signals generated by the sensor. Thus, in use, only light that has been reflected from the surface area of the injection device can influence signals generated by the sensor. This is because the field of view of the sensor is restricted or limited by the shield such that the field of view of the sensor is entirely directed at the surface area of the injection device in use. This provides that any ambient light which has been reflected from a portion of the injection device outside the surface area of the injection device, mentioned in the foregoing aspect, cannot influence signals generated by the sensor.

A lens may not be provided in the field of view of the sensor. In other words, the supplemental device may be provided with a lens-free path between an object in the field of view of the sensor (e.g. an injection device) and the sensor. For example, the supplemental device may be provided with a lens-free path between the surface area of the injection device (i.e. the area of the injection device in the field of view of the sensor when the injection device and supplemental device are coupled to one another) and the sensor, when the supplemental device is attached to the injection device. Advantageously, this simplifies the supplemental device thereby making it cheaper to manufacture while simultaneously improving the reliability thereof.

A component with optical power may not be provided in the field of view of the sensor. In other words, all transparent components in the field of view of the sensor may have an optical power of zero. In further words, the supplemental device may be absent of any component with optical power between the field of view of the sensor and the sensor. For example, the supplemental device may be absent of any component with optical power between the surface area of the injection device (i.e. the area of the injection device in the field of view of the sensor when the injection device and supplemental device are coupled to one another) and the sensor, when the supplemental device is attached to the injection device.

The supplemental device may further comprise a housing. The housing may provide protection for the other components of the supplemental device. The housing may comprise at least one transparent portion. A transparent portion may be arranged in the field of view of the sensor. All transparent components between the surface area of the injection device and the sensor in use may have an optical power of zero. This provides that the sensor may be protected from dirt without unduly increasing the cost of manufacture of the supplemental device.

The shield may be located directly between the light source and the sensor. This provides that light from the light source cannot become directly incident on the sensor.

An aperture defined by the shield may be located opposite the sensor, and the aperture may be configured to restrict or limit the field of view of the sensor. The aperture may have a centre that is substantially aligned with a centre of the field of view of the sensor.

The shield may comprise a member that defines the aperture. The member may be substantially frustum-shaped and the aperture may be formed at the peak of the frustum. Alternatively the aperture may be defined by two side walls of the shield.

The light source may comprise a plurality of LEDs that are arranged around the shield, or the light source may comprise a plurality of LEDs that are arranged adjacent to one another substantially in a straight line. Each of the LEDs in said plurality of LEDs may be configured to emit a different wavelength of light.

The processor may be configured to cause each of the LEDs to emit light for respective exposure times. This may be used to reduce the length of time for which LEDs are switched on in use, thereby reducing power consumption and increasing battery life of the supplemental device.

The plurality of LEDS may be controlled by the processor to sequentially emit light of the respective wavelengths.

The supplemental device may be configured for recording information about doses of medicament ejected from the injection device, in use.

The supplemental device may be attached to an injection device in use, such that the supplemental device obstructs a dosage window of the injection device.

The supplemental device may further contain at least one optical sensor for gathering information indicative of what is displayed in the dosage window.

DETAILED DESCRIPTION

In the following, embodiments of the present invention will be described in the context of a supplemental device for determining an amount of dose dialled, or an amount of dose dispensed, by an injection device. Such a supplemental device may be provided with optical character recognition (OCR) functionality for making such a determination. The present invention is however not limited to such application and may equally well be deployed with supplemental devices of other kinds, for example a supplemental device that merely displays a dialled dose amount in larger format than it appears on the number sleeve of an injection device.

The injection device can for example be a pen-like injection device. Devices of this kind are well known in a self-medication environment, where a user or patient administers a dose of medicament. Re-usable and disposable variants are known from pen-like injection devices. These kinds of injection devices are typically hand-held when in use. Pen-like injection devices can be carried around by the user, for example in a pocket, a wallet-like etui, etc.

The supplemental device according to the invention is configured for attachment to an injection device. When in use, the injection device with the attached supplemental device is hand-held.

When attached to an injection device, the supplemental device may partly cover the injection device. The supplemental device may cover a part of the injection device that comprises the dose display of the injection device.

The supplemental device may further be configured for recording information about the doses that are administered from the injection device to which it is attached in use, or in other words the supplemental device may be configured for recording information indicative of the quantity of medicament ejected from the injection device.

Figure 1:
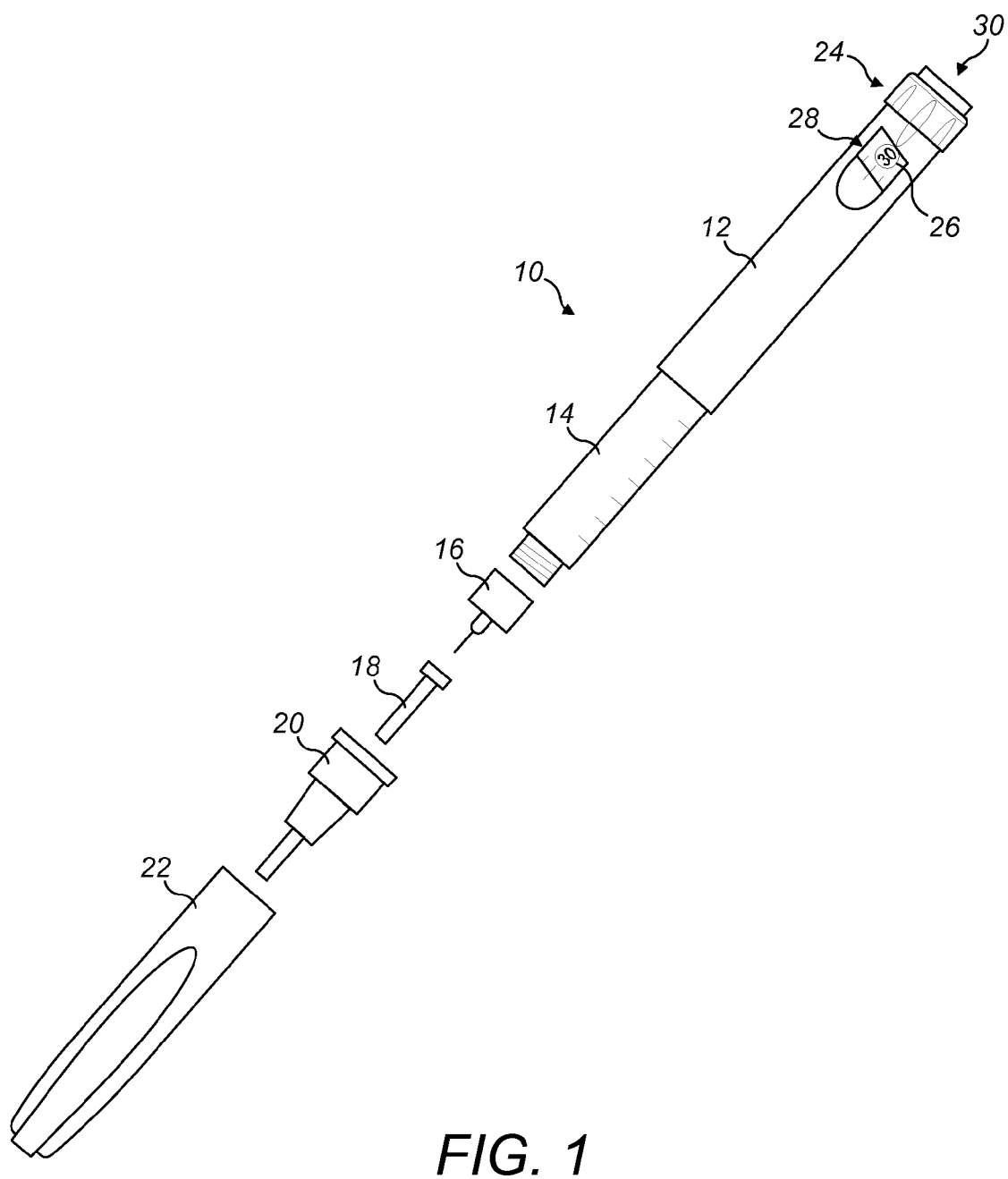
FIG. 1 is a schematic view of an exemplary injection device.

FIG. 1 is an exploded view of an injection device 10, which may for instance represent the Solostar™ injection pen sold by Sanofi.

The injection device 10 of FIG. 1 is a pre-filled, disposable injection pen that comprises a housing 12 and contains an insulin container 14, to which a needle 16 can be affixed. The needle 16 is protected by an inner needle cap 18 and an outer needle cap 20, which in turn can be covered by a cap 22. An insulin dose to be ejected from injection device 10 can be selected by turning the dosage knob 24 (this act may be referred to as dialling an insulin dose). A marker comprising a number 26 indicative of the selected dose (the dialled dose) is displayed via dosage window 28 in multiples of International Units (IU) for instance. An example of a dialled dose displayed in the dosage window 28 may be 30 IUs, as shown in FIG. 1.

The numbers 26 displayed in the dosage window 28 are printed on a sleeve (known as the number sleeve 17) contained in the housing 12 and which mechanically interacts with a piston inside the insulin container 14. When needle 16 is inserted into the skin of a patient and the injection button 30 is pushed, an amount of insulin corresponding to the dialled quantity displayed in the display window 28 is ejected from the injection device 10. During the course of the injection, as insulin leaves the injection device 10, the number sleeve 17 rotates. This causes the number 26 displayed in the dosage window 28 to change in accordance with the dialled amount of insulin yet to be dispensed. In other words, during the course of an injection the numbers 26 that successively align with the dosage window 28 are caused to count down.

Figure 2:
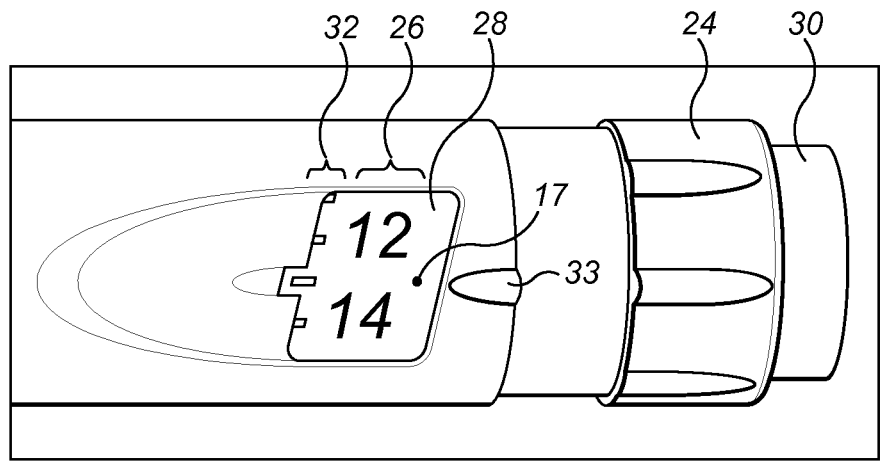
FIG. 2 is an enlarged view of an end of the injection device in FIG. 1.

FIG. 2 shows the dosage window 28 after 17 IUs of insulin have been delivered from the injection device 10 during the course of the injection in the preceding paragraph.

Figure 3:
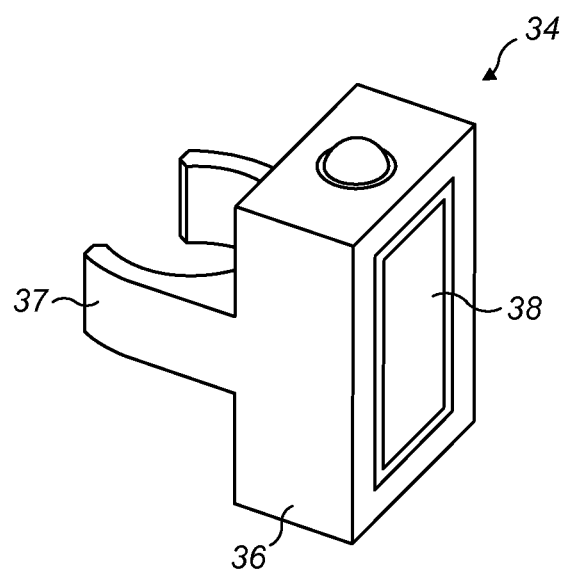
FIG. 3 is a schematic view of a supplemental device according to one embodiment of the present invention.

FIG. 3 is a schematic illustration of a supplemental device 34 which may be releasably attached to an injection device such as the one depicted in FIG. 1. The supplemental device 34 comprises a housing 36 which is provided with a mating unit, coupling unit or connector 37 for embracing the housing 12 of an injection device 10. In particular the connector 37 may be configured to snap-fit onto the housing 12 of an injection device 10 in such a way that the device 34 can be subsequently removed therefrom. The connector 37 need not however be of the snap-fit variety and other arrangements may alternatively be suitable for coupling the supplemental device 34 to an injection device.

Figure 4:
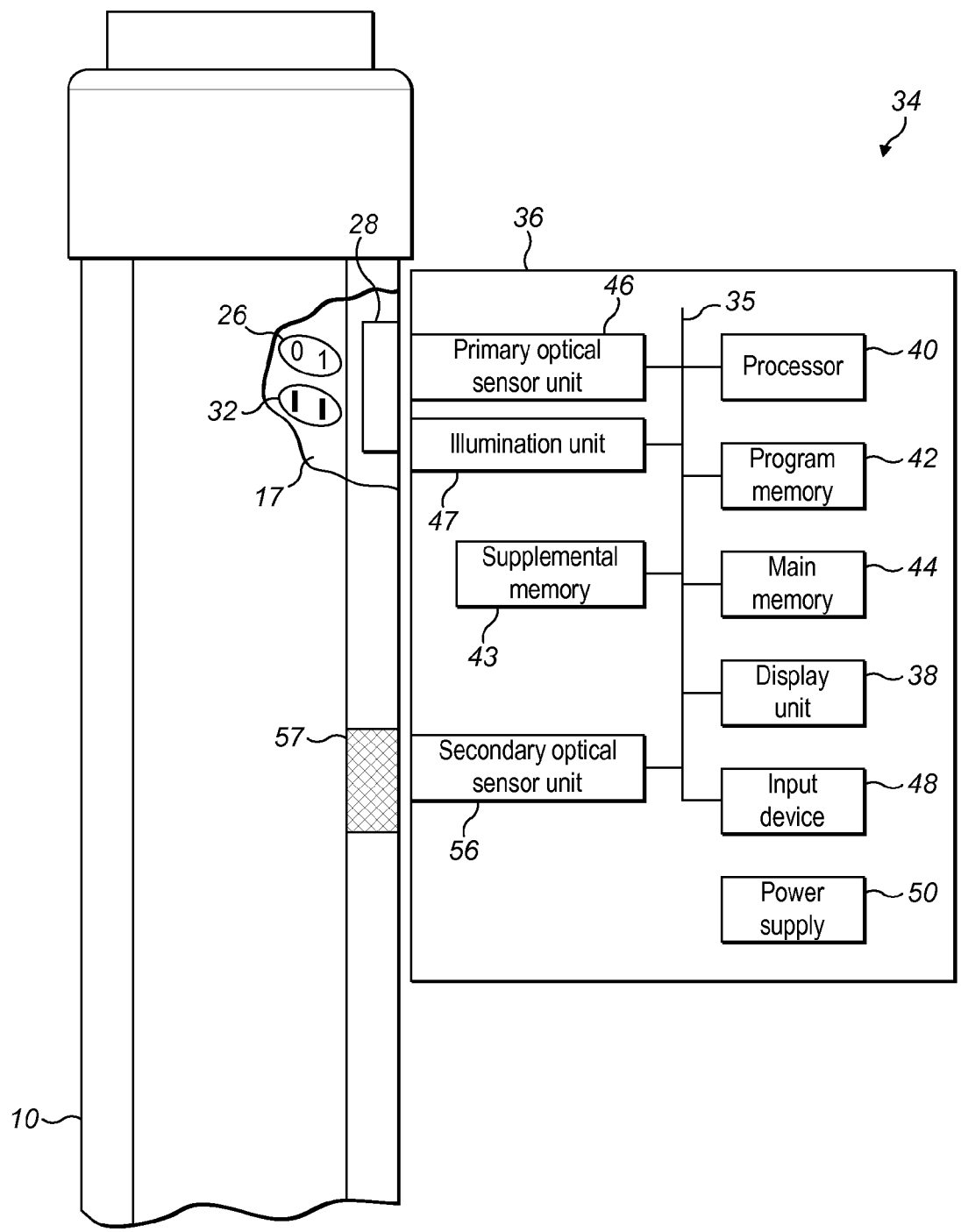
FIG. 4 is a schematic internal view of the supplemental device in FIG. 3.

When coupled to an injection device 10, the supplemental device 34 obstructs the dosage window 28 (as in FIG. 4). The supplemental device 34 contains at least one optical sensor for gathering information from the injection device 10. In particular the optical sensor(s) is(are) caused to gather information indicative of what is displayed in the dosage window 28. This gathered information is then capable of being processed for generating a dose history database. Such a dose history database may include records containing information about the various times at which insulin doses are administered and the quantity of insulin administered during each dose. The gathered information may also be processed for the purpose of displaying numbers 26 aligned with the dosage window 28 in larger format, for example by displaying numbers on a display unit which are larger than those provided on the number sleeve 17. This improves the readability of the amount of dose dialled or, in the case of an injection, the dialled dose amount yet to be delivered.

FIG. 4 illustrates an internal schematic view of the supplemental device 34 in a state where it is coupled to an injection device 10.

Within the housing 36 of the supplemental device 34, a variety of components are located and coupled together by a system bus 35. One such component includes a processor 40. Program memory 42 and main memory 44 are also coupled to the system bus 35. The processor 40 executes program code (e.g. software or firmware) stored in the program memory 42 and uses the main memory 44 to store intermediate results. The supplemental device 34 also comprises a supplemental memory 43 for storing the aforementioned dose history database. Program memory 42 may for instance be non-volatile memory such as Read-Only Memory. Main memory 44 may for instance be a volatile memory such as Random Access Memory, DRAM or SDRAM and supplemental memory 43 may for instance be Flash memory or an EEPROM or may comprise a memory card coupled to the system bus 35 via an interface such as a USB-type connection.

A primary optical sensor unit 46, also coupled to the system bus 35, is used to generate signals containing information indicative of what is displayed in the dosage window 28. The processor 40 may use these signals to determine delivered doses and generate the dose history database. The processor 40 may achieve this by executing an optical character recognition application to determine, from signals sent by the primary optical sensor unit 46, which number(s) 26 is(are) aligned with the dosage window 28. On the basis of such information the processor 40 then determines how much insulin has been dialled or, in the case of an injection, the dialled amount of insulin that remains to be delivered (or has already been delivered during the course of the injection).

Other components which may be coupled to the system bus 35 include an illumination unit 47, a display unit 38 and an input device 48. Such an illumination unit 47 may include one or more LEDs and may be controlled by the processor 40 to illuminate information displayed in the dosage window 28. An input device 48 (for example, a keypad) may be utilised by a user to interact with the supplemental device 34. Such an input device 48 may for instance be used to select one or more options displayed on a display unit 38. In some embodiments a display unit 38 may be provided with touch-screen functionality thus enabling it to function as both an output device and the input device 48.

A power supply source 50 (for example a battery) is for powering the various components of the supplemental device 34.

In some embodiments, the primary optical sensor unit 46 may comprise a camera and the processor 40 may cause a display unit 38 to show information, e.g. images, that represent the number sleeve 17 as it appears in the field of view of the camera.

Regardless of the particular combination of features provided, a supplemental device 34 further comprises a secondary optical sensor unit 56 coupled to the system bus 35. The processor 40 uses the secondary optical sensor unit 56 to determine characteristics of a surface portion 57 located on an injection device 10. The surface portion 57 may comprise a part of a label or a part of the outer casing of the injection device 10 for instance. The surface portion 57 may thus be fixed, adhered or printed onto the injection device 10 or may comprise an integral part of the outer casing of the injection device 10. This is useful because injection devices 10 having different properties may be provided with different kinds of surface portions 57. In particular, injection devices 10 containing different types of medicament (e.g. different types of insulin) may have different coloured surface portions 57. A supplemental device 34 is thus able to determine what type of medicament an injection device 10 contains by analysing characteristics of its surface portion 57 or a part of the surface portion 57, for instance a part of a label that includes details of the injection device 10 such as brand information.

As will be explained in more detail below, the processor 40 causes the secondary optical sensor unit 56 to illuminate the surface portion 57 with light of different wavelengths. The secondary optical sensor unit 56 generates signals indicative of the intensity of light, of each respective wavelength, reflected by the surface portion 57. These signals are then used by the processor 40 to determine a property of the injection device 10. This is enabled by the processor 40 comparing the reflection characteristics of the surface portion 57 with one or more records, each of which associates a different property of an injection device with a respective reflection response. Different coloured surface portions 57 reflect different amounts of light across a spectrum of different wavelengths. Thus by determining the reflection characteristics of a surface portion 57 having a particular colour, a property associated with that colour in one of the aforementioned records can be determined. An example of one such property may be an injection device type or a medicament type.

As already mentioned, an implementation of the present invention is to distinguish medical devices having different coloured surface portions 57, e.g. depending on the kind of medication they contain. Alternatively, the surface portions 57 could be coloured differently depending on the type of insulin the respective devices contain.

For example, injection devices 10 containing short-acting insulin may be provided with a first coloured, e.g. red coloured, surface portion 57 whereas injection devices 10 containing long-acting insulin may be provided with a second coloured, e.g. blue coloured, surface portion 57. A first record which associates short-acting insulin with reflection characteristics of the first colour, the colour red in this example, and a second record which associates long-acting insulin with reflection characteristics of the second colour, the colour blue in this example, may be accessed by the processor 40 for determining what type of insulin is contained within a particular injection device 10. More specifically, the reflection characteristics of the surface portion 57 of a particular injection device 10 are compared with those in the foregoing records. This enables the processor 40 to determine what insulin type has been associated with the colour of the surface portion 57. If the surface portion 57 is blue, for instance, then the processor 40 determines that the injection device 10 contains long-acting insulin.

It will be appreciated that injection devices containing other types of insulin or other types of medicament may be provided with different coloured surface portions. Following on from the example in the foregoing paragraph such colours should be other than red or blue. Corresponding records associating reflection characteristics of the various surface portion colours with respective types of insulin or other medicament may be provided for enabling a processor to determine what substance is contained by an injection device upon analysing reflection characteristics of its surface portion (or a part thereof).

Details of the secondary optical sensor unit 56 will now be explained in more detail with reference to FIG. 5.

The secondary optical sensor unit 56 comprises a plurality of light sources 58 such as LEDs for illuminating a surface portion 57 of an injection device in use. Light from the LEDs exits from the supplemental device 34 and becomes incident on the surface portion 57. Each light source 58 may be configured to emit light of a different wavelength. For example the first, second and third light sources 58a, 58b, 58c in FIG. 5 are configured to emit first, second and third wavelengths $\lambda_1$, $\lambda_2$, $\lambda_3$ of light respectively. However, a plurality of light source groups may be provided instead, the light sources in each group being configured to emit light of the same wavelength.

Light of the first wavelength $\lambda_1$ emitted by the first light source 58a may be red, blue or green. Light of the second wavelength $\lambda_2$ emitted by the second light source 58b may be another of red, blue or green. Light of the third wavelength $\lambda_3$ emitted by the third light source 58c may be the remaining of red, blue or green.

In some embodiments, light of the first wavelength $\lambda_1$ is red, light of the second wavelength $\lambda_2$ is blue and light of the third wavelength $\lambda_3$ is green. Throughout this specification, red light has a wavelength between approximately 620 nm and 740 nm, blue light has a wavelength between approximately 450 nm and 495 nm and green light has a wavelength between approximately 520 nm and 570 nm.

The examples of the first to third wavelengths $\lambda_1$, $\lambda_2$, $\lambda_3$ outlined in the foregoing paragraph are merely exemplary. Such wavelengths may be of any value so long as they are different from one another. Additionally, the emissions of a light source 58 may not be solely at one discrete frequency but may instead be spread over a relatively narrow band of frequencies, which may overlap to some extent with the band of another light source 58. Also, one or more of the first to third wavelengths $\lambda_1$, $\lambda_2$, $\lambda_3$ may be outside the visible spectrum and could be infrared or ultraviolet for instance.

Referring again to FIG. 5, the secondary optical sensor unit 56 further comprises a sensor 60 for generating sensor outputs. Such sensor outputs are indicative of the respective intensities of light of different wavelengths reflected from the surface portion 57. For instance following an exposure time, during which reflected light of a particular wavelength is incident on the sensor 60, the sensor 60 generates a signal indicative of the intensity of reflected light of that particular wavelength on the sensor 60 during that particular exposure time. In use, different wavelengths of light are caused to become incident on the sensor 60 for respective exposure times. The sensor 60 generates signals indicative of the intensity of reflected light of each particular wavelength on the sensor 60 during the respective exposure times.

Figure 5:
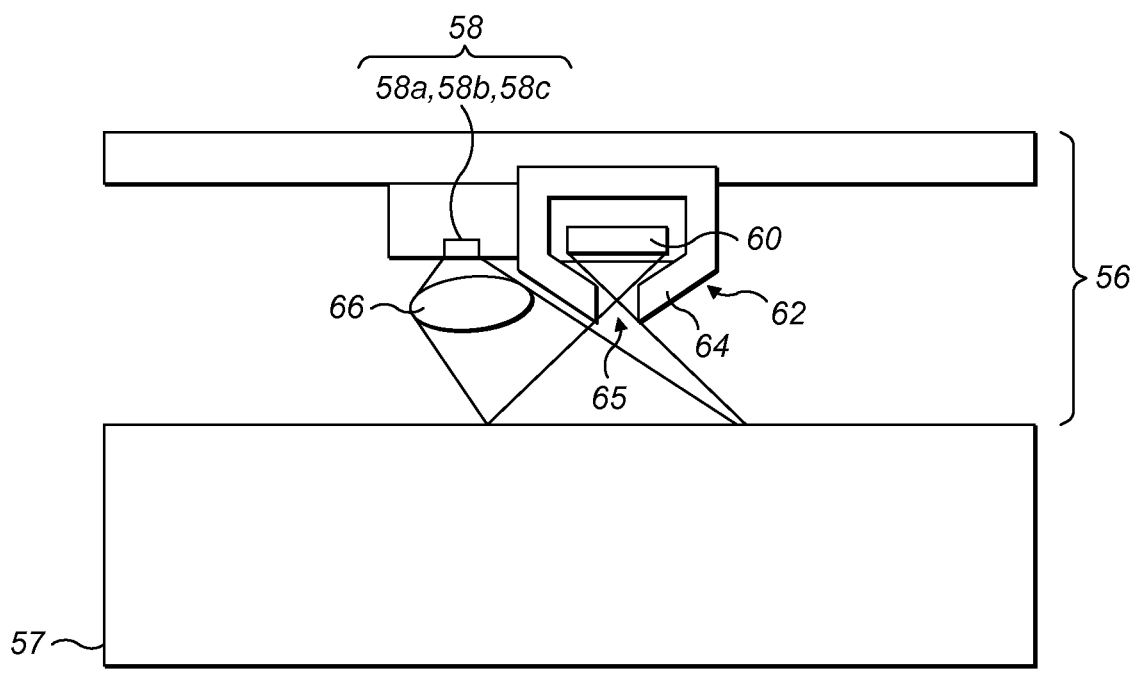
FIG. 5 is a schematic cross-sectional diagram of a secondary optical sensor unit.

In the example of FIG. 5, the processor 40 causes the first to third light sources 58a to 58c to respectively emit light of the first to third wavelengths $\lambda_1$ to $\lambda_3$ for respective exposure times $t_1$ to $t_3$. The light sources 58a to 58c are controlled to sequentially emit light of the first to third wavelengths $\lambda_1$ to $\lambda_3$. Therefore following a first exposure time $t_1$, during which reflected light of the first wavelength $\lambda_1$ is incident on the sensor 60, the sensor 60 generates a first signal S1 (described in the next paragraph). Following a second exposure time $t_2$, during which reflected light of the second wavelength $\lambda_2$ is incident on the sensor 60, the sensor 60 generates a second signal S2. Furthermore following a third exposure time $t_3$, during which light of the third wavelength $\lambda_3$ is incident on the sensor 60, the sensor 60 generates a third signal S3.

The first signal S1 mentioned in the foregoing paragraph is indicative of the intensity of reflected light of the first wavelength $\lambda_1$ incident on the sensor 60 during the first exposure time $t_1$. Similarly the second signal S2 is indicative of the intensity of reflected light of the second wavelength $\lambda_2$ incident on the sensor 60 during the second exposure time $t_2$. The third signal S3 is indicative of the intensity of reflected light of the third wavelength $\lambda_3$ incident on the sensor 60 during the third exposure time $t_3$.

A supplemental device 34 is calibrated such that if the surface portion 57 (or at least the part thereof from which light reflects onto the sensor 60) is a neutral colour (e.g. grey) then the respective signals generated by the sensor 60, in response to detecting light of the different wavelengths, are substantially similar. More specifically in such circumstances the respective signals generated by the sensor 60, which are indicative of the intensity of reflected light of each particular wavelength on the sensor 60 during the respective exposure times, are substantially similar.

In the example in FIG. 5, the supplemental device 34 is configured such that if the surface portion 57 (or at least the part thereof from which light reflects onto the sensor 60) is a neutral colour (e.g. grey) then the first to third signals S1 to S3 generated by the sensor 60 in use will be substantially similar. Such signals S1 to S3 are deemed to be substantially similar if they are indicative that during first to third exposure times $t_1$ to $t_3$ the intensity of reflected light of the first to third respective wavelengths $\lambda_1$ to $\lambda_3$ on the sensor 60 is substantially similar.

Calibrating a supplemental device 34 to perform in this manner involves altering the duration of one or more of the exposure times of light of the respective wavelengths (exposure times $t_1$ to $t_3$ in the example of FIG. 5). The respective durations of the calibrated exposure times are stored by the supplemental device 34, for example in the program memory 42. The supplemental device 34 utilises these calibrated exposure time durations when in use for the respective exposure times of light of different wavelengths. Advantageously, calibrating a supplemental device 34 in this way minimises the total amount of time for which the light sources 58 are activated in use. This reduces the power consumption of the supplemental device 34, thereby prolonging battery life.

Referring again to FIG. 5, the secondary optical sensor unit 56 in a supplemental device 34 is further provided with a shield 62, which can also be termed a screen or a baffle. This shield 62 is opaque to light of the wavelengths emitted by the light sources 58. For example, in FIG. 5 the shield 62 is opaque to light of at least the first, second and third wavelengths $\lambda_1$, $\lambda_2$, $\lambda_3$.

The shield 62 prevents light emitted by the light sources 58 becoming directly incident on the sensor 60. An aperture 65 defined by the shield 62 is in the field of view of the sensor 60. The aperture 65 restricts or limits the field of view of the sensor 60, as is discussed in more detail below. The field of view of the sensor 60 is defined by the aperture 65. Light that has been reflected from the surface portion 57 in the field of view of the sensor 60 (as defined by the aperture 65) enters the supplemental device 34, travels through the aperture 65 and becomes incident on the sensor. In some embodiments said light may enter the supplemental device through the aperture 65.

Figure 5A:
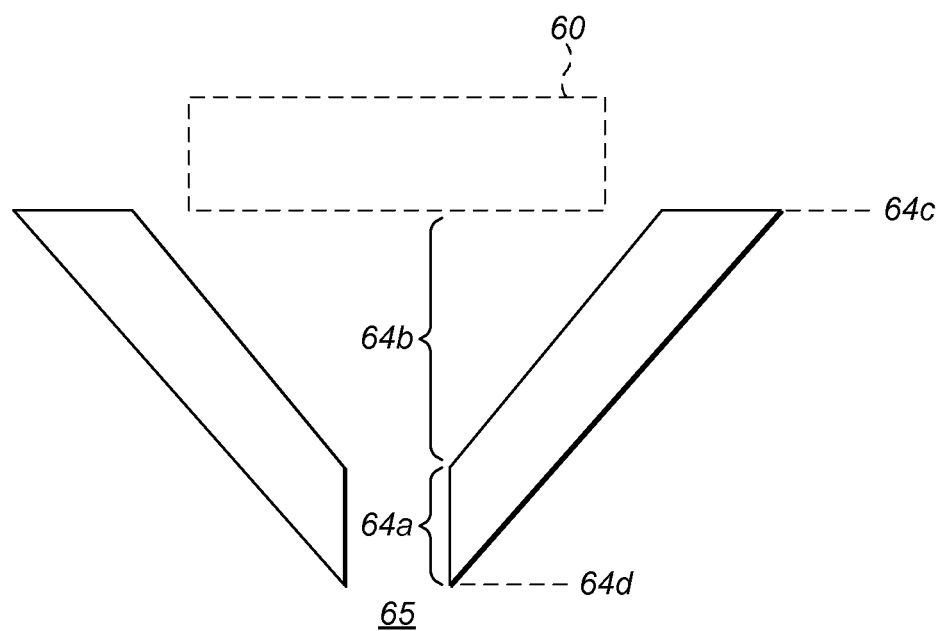
FIG. 5a is a schematic cross-sectional view of part of the shield in FIG. 5.

The centre of the aperture 65 is substantially aligned with the centre of the field of view of the sensor 60. The aperture 65 is formed at the peak of a hollow frustum-shaped blocking member 64 of the shield 62. The hollow frustum-shaped blocking member 64 of the shield 62 does not have a constant cross-sectional width. As shown in FIG. 5, the internal diameter of the hollow frustum-shaped blocking member 64 increases towards the sensor 60. With particular reference to FIG. 5a, the frustum-shaped blocking member 64 comprises a neck 64a with a constant cross-sectional width and a chamber 64b which tapers from the neck 64a and increases in width towards the sensor 60.

In use, the surface portion 57 of an injection device 10 is caused to be aligned with both the aperture 65 and the sensor 60 as shown in FIGS. 4 and 5. This occurs when the connector 37 (see FIG. 3) is mated with (coupled to) the injection device 10. Such alignment provides that the surface portion 57 (or at least a section of the surface portion) is in the field of view of the sensor 60, in use.

In particular, the aperture 65 defined by the hollow frustum-shaped blocking member 64 of the shield 62 provides that only the relevant section of the surface portion 57 is in the field of view of the sensor 60, in use. Moreover, because of the arrangement of the aperture 65 defined by the hollow frustum-shaped blocking member 64 of the shield 62 in relation to the relevant section of the surface portion 57, this is achieved without the use of any lens in the path between the sensor 60 and the relevant section of the surface portion 57. Put another way, the supplemental device 34 is provided with a lens-free path between the surface portion 57 of the injection device 10 and the sensor 60. Thus, the supplemental device 34 is absent of any component with optical power between the surface portion 57 of the injection device 10 and the sensor 60. In other words, the supplemental device 34 is absent of any component between the surface portion 57 of the injection device 10 and the sensor 60 that is capable of focussing light. Put yet another way, all transparent components between the surface portion 57 of the injection device 10 and the sensor 60 have an optical power (focussing ability) of zero. Zero optical power gives rise to no convergence or divergence of light. No such transparent components are shown in the Figures, although in practice a transparent, planar protection window may be included to protect the internal components of the supplemental device 34 from the ingress of contaminant materials.

The supplemental device 34 is configured to engage with the injection pen 1 such that the surface portion 57 is a relatively small distance away from the sensor 60. Moreover, the mating arrangement is such that the distance is substantially constant when the supplemental device 34 is engaged with the injection pen 1.

The area of the surface portion that is in the field of view of the sensor is defined by a number of factors, including the shape and size of the aperture 65, the location of the aperture 65 relative to the sensor 60, the size and shape of the active part of the sensor 60 and the distance between the surface portion 57 and the aperture 65. The various features are configured to provide a region of approximately 0.5 mm square of the surface portion 57 within the field of view of the sensor 60 when the supplemental device 34 is properly engaged with the injection pen 1. The various features are configured such that the area of the surface portion 57 that is within the field of view is always within acceptable limits even if the separation between the relevant parts of the supplemental device 34 and the injection device 1 increases or decreases by a modest amount.

The light sources 58 and the lens 66 may be configured such as to illuminate a greater area of the surface portion 57 than is within the field of view of the sensor for all separations between the relevant parts of the supplemental device 34 and the injection device 1 within a modest amount of the intended separation.

The light sources 58 are not aligned with the sensor 60 and the aperture 65. This provides that the light sources 58 are not in the field of view of the sensor 60. Thus when the processor 40 causes the light sources 58 to emit light, only light emitted by the light sources 58 that is reflected from the section of the surface portion 57 in the field of view of the sensor 60 is detected. More specifically, in use light that is reflected from the surface portion 57 in the field of view of the sensor 60 travels through the aperture 65 prior to becoming incident on the sensor 60.

This improves the reliability of the supplemental device 34 because light (from an ambient source for example) that has not been reflected from the surface portion 57 in the field of view of the sensor 60 cannot influence signals generated by the sensor 60. Reflection response analysis of the surface portion 57 in the field of view of the sensor 60 is thereby improved. This reduces the likelihood that a property associated with a particular reflection response will be incorrectly identified. For example the colour of the surface portion 57 in the field of view of the sensor 60 may be determined and then compared with information pre-stored in a memory of the supplemental device 34 which associates particular colours with respective injection device properties e.g. types of insulin. In this example by improving the reliability of colour detection/determination of the supplemental device 34 then it is less likely that an incorrect type of insulin will be associated with the determined colour of the surface portion 57 under analysis. This could be potentially life saving if, for instance, the supplemental device 34 sounds an audible alarm or indicates a visual warning when an injection device to which it is attached is determined to contain insulin of a different type to that which a user is supposed to inject themselves with; whereby information indicative of the prescribed type of insulin is stored in a memory of the supplemental device 34.

The structure of the shield 62 will now be explained in slightly more detail with reference to FIG. 5a. It is apparent from FIG. 5a that the portion of the shield 62 which defines the aperture 65 extends between a first end 64c at the base of the chamber 64a and a second end 64d at the opposite end of the neck 64a. The second end 64d is further from the sensor 60 than the first end 64c. It is also apparent that opposite sides of the first end 64c are displaced further apart than opposite sides of the second end 64d. More specifically, the portion of the shield 62 which defines the aperture 65 is substantially the shape of a frustum, the aperture 65 being present at the peak of the frustum.

In some embodiments the outer surface of the frustum-shaped portion substantially defines a circle. In such embodiments the frustum-shaped portion is substantially the shape of a conical frustum. In other embodiments the outer surface of the frustum-shaped portion substantially defines a polygon. In such embodiments the frustum-shaped portion may be substantially the shape of a square frustum or a pyramidal frustum for example.

Figure 5B:
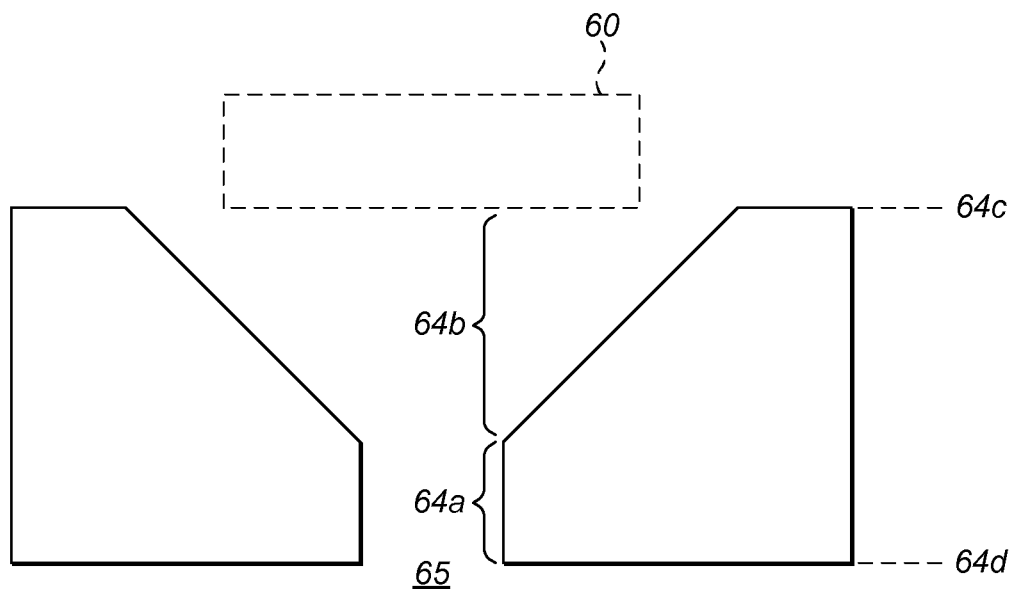
FIG. 5b is a schematic cross-sectional view of part of a shield according to another embodiment.

It is however not necessary that a hollow frustum-shaped blocking member 64 is used as part of the shield 62. In FIG. 5b, the external surface of the portion of the member 64 of the shield 62 which defines the aperture 65 is substantially square shaped.

Figure 5C:
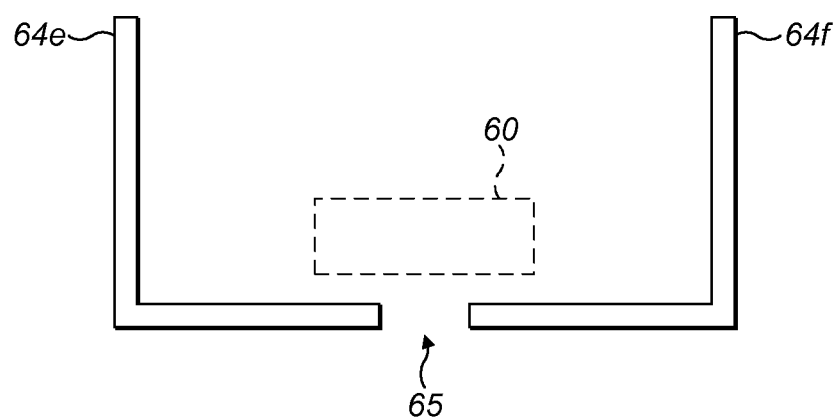
FIG. 5c is a schematic cross-sectional view of part of a shield according to a further embodiment.

Furthermore, it is not necessary for the shield 62 to have two portions of different cross-sectional width such as the chamber 64a and the neck 64b. Looking at FIG. 5c for example, the aperture 65 defined by the shield 62 may have instead have a constant cross-sectional width along its length and open into a volume defined by two side walls 64e and 64f.

Figure 6:
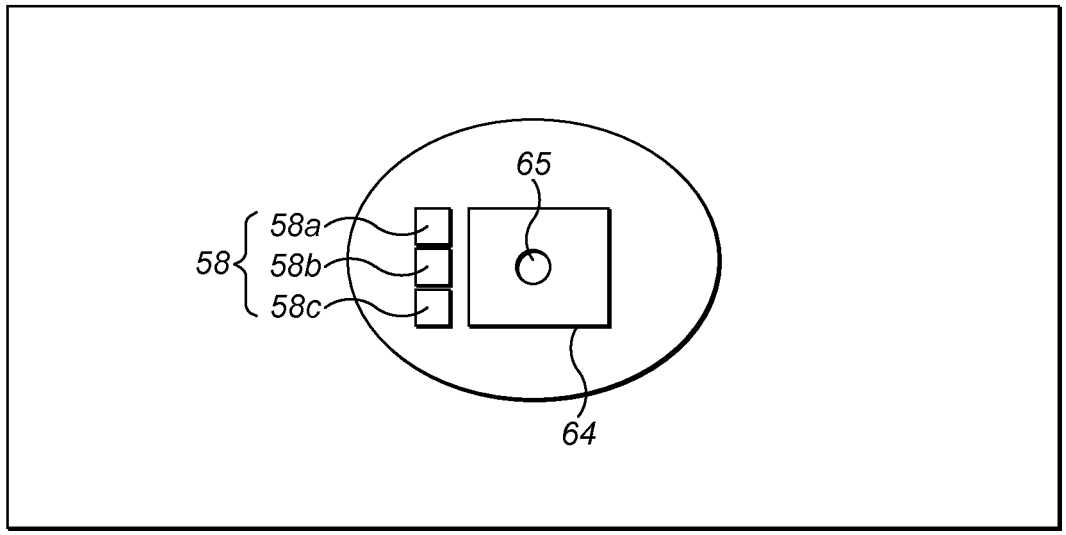
FIG. 6 is a schematic diagram of the underside of the secondary optical sensor unit in FIG. 5.

FIG. 6 shows that respective light sources (e.g. those denoted 58a, 58b and 58c) may be arranged adjacent to one another for example in a line. Respective light sources may however be distributed around the hollow frustum-shaped blocking member 64. For example one or more light sources may be located to the left of the shield 62 in FIG. 6 and one or more other light sources may be located to the right of the shield 62 in FIG. 6. Also, in some embodiments light sources may be arranged in a ring, square, rectangle or triangle around the shield 62.

One or more lenses 66 may be provided for focussing light emitted by the light sources 58 onto the surface portion 57 or a section thereof in the field of view of the sensor 60. Furthermore one or more lenses (not shown) may be provided for focussing light reflected by the surface portion 57 onto the sensor 60, however this is also not necessary and advantageously no such lenses are present. Advantageously, this improves the reliability of the reflection response analysis capable of being performed by a supplemental device 34 because light that has not been reflected from the surface portion 57 cannot influence signals generated by the sensor 60. In particular, a supplemental device 34 is configured such that, in use, only light emitted from the light sources 58 and reflected by the surface portion 57 is able to become incident on the sensor 60.

How the secondary optical sensor unit 56 is used by the processor 40 to determine a property of an injection device 10 will now be explained with particular reference to the example in FIG. 5. The processor 40 controls the first, second and third light sources 58a, 58b, 58c sequentially to illuminate the surface portion 57 with light of first, second and third wavelengths $\lambda_1$, $\lambda_2$, $\lambda_3$ respectively for respective calibrated exposure times $t_1$, $t_2$, $t_3$. Upon such illumination the sensor 60 generates first, second and third signals S1, S2 and S3 respectively. These first to third signals S1 to S3 are (as aforementioned) indicative of the intensity of reflected light incident on the sensor 60 during the respective exposure times.

The processor 40 uses the first to third signals S1 to S3 to obtain first to third respective values A to C. In other words, the processor 40 assigns a numerical value to each of the first to third signals S1 to S3. The respective magnitudes of the first to third values A to C are proportional to a property of the first to third respective signals S1 to S3 that changes in accordance with the intensity of reflected light incident on the sensor 60 during a particular exposure time.

In the example that the sensor 60 is a photodiode for instance, the magnitude of an output voltage signal generated by the photodiode depends on the intensity of incident light during a particular exposure time. Thus when light of the first wavelength $\lambda_1$ for example is incident on the photodiode for an exposure time $t_1$, if the magnitude of the output voltage signal S1 is low then the corresponding first value A obtained by the processor 40 will be low also. However if the magnitude of the output voltage signal S1 generated is higher due to an increased intensity of light of the first wavelength $\lambda_1$ during the exposure time $t_1$, then the first value A obtained by the processor 40 will also be higher. The same applies in respect of the second and third values B and C obtained using second and third output voltage signals S2 and S3 generated when the photodiode is illuminated with light of the second and third wavelengths $\lambda_2$ and $\lambda_3$ respectively.

The first to third values A to C might be indicative of power per unit area (W/m$^2$). The first value A might be indicative of the power per unit area of light of the first wavelength $\lambda_1$ on the sensor 60 during a first exposure time $t_1$. Similarly the second and third values B and C might be indicative of the power per unit area of light of the second and third respective wavelengths $\lambda_2$ and $\lambda_3$ on the sensor 60 during second and third respective exposure times $t_2$ and $t_3$. The first to third values A to C might not however be indicative of power per unit area and might instead be indicative of another quantity, provided that the first to third values A to C are indicative of the same quantity. For example the first to third values A to C may be indicative of the total amount of electromagnetic energy (Joules) incident on the sensor 60 during respective exposure times $t_1$ to $t_3$.

The processor 40 performs a calculation using the first and second values A and B to provide a fourth value D. The processor 40 does not use the third value C when performing this calculation. Calculating the value of D comprises determining the output of a function f(A, B). Thus mathematically f(A, B)=D, wherein f(A, B) may comprise at least a division in which A is in the numerator and B is in the denominator. For example calculating the value of D may involve determining at least the value of A/B or A/(A+B).

The processor 40 also performs another calculation in which the third value C is used to provide a fifth value E. Calculating the value of E comprises determining the output of a function f(C). Thus mathematically f(C)=E, wherein f(C) comprises one or more calibration factors which will be discussed later.

Having determined the fourth and fifth values D and E the processor 40 determines a property of the injection device 10 it is analysing. This is enabled by the processor 40 comparing the determined fourth and fifth values D and E with a list of records. These records respectively associate different information with different combinations of predetermined fourth and fifth values D and E.

The predetermined fourth and fifth values D and E in a particular record are those that the processor 40 determines if the surface portion 57 of an injection device 10 (or at least the part thereof in the field of view of the sensor 60) is a particular colour. This is how providing an injection device 10 with a surface portion 57 of a particular colour enables a supplemental device 34 to determine a property of the injection device 10. More specifically, providing the surface portion 57 with a particular colour results in the processor 40 determining a particular combination of fourth and fifth values D and E that are only determined when the analysed surface portion 57 is that particular colour. Comparing these values with the one or more records accessible by the processor 40 enables the processor to determine which particular property has been associated with those particular fourth and fifth values D and E.

In practice, providing the surface portion 57 of an injection device with a particular colour may not result in the processor 40 determining particular fourth and fifth values D and E exactly. Instead, such values may only be determined within a range of accuracy that is influenced by the manufacturing tolerances of the supplemental device assembly process, and also, the efficiency of the various components thereof for example the sensor 60 and light sources 58. As such the records previously mentioned may associate predetermined ranges of fourth and fifth values D and E with particular injection device properties (instead of associating exact values with injection device properties).

It will be appreciated that information indicative of different injection device types may be included in respective records. In other words, different injection device types may be associated with different combinations of predetermined fourth and fifth values D and E (or ranges thereof). In this implementation, different types of injection devices 10 may be provided with different coloured surface portions 57 for enabling a supplemental device 34 to determine the type of injection device 10.

It will also be appreciated that information indicative of different types of medicament (e.g. different types of insulin) may be included in respective records. In other words, different types of medicament may be associated with different combinations of predetermined fourth and fifth values D and E (or ranges thereof). In this implementation, injection devices 10 may be provided with different coloured surface portions 57 for enabling a supplemental device 34 to determine the type of medicament contained within the injection device 10.

Information concerning the type of medicament which a person injects themselves with may be stored in the aforementioned dose history database. Also, a supplemental device 34 may be configured to alert a user when an injection device 10 is determined to contain other than a pre-specified type of medicament. Such an alert may comprise the sounding on an audible alarm or the presentation of a visual indication on a display unit.

Figure 7:
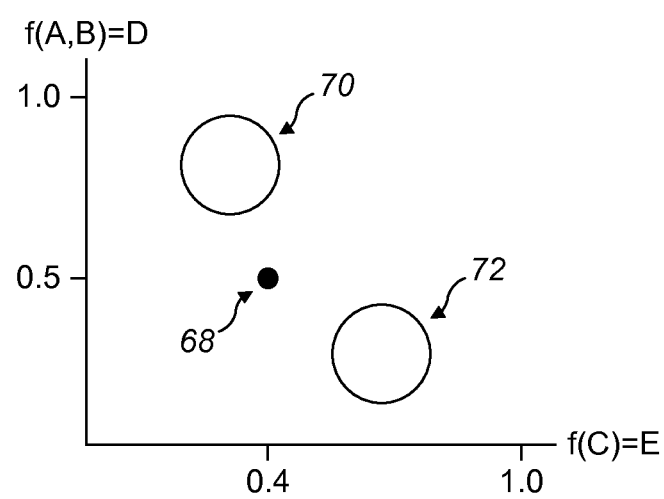
FIG. 7 is a graphical representation of fourth and fifth values that may be determined by the supplemental device in FIGS. 3 and 4.

FIG. 7 is a graphical representation of the foregoing. The vertical axis represents possible magnitudes of the fourth value D, which is the output of the function f(A, B). The horizontal axis represents the possible magnitudes of the fifth value E, which is the output of the function f(C). Since different coloured surface portions 57 are associated with different fourth and fifth values D and E, different coloured surface portions 57 are associated with different locations in the space shown in FIG. 7.

In the previous discussion regarding records it was stated that respective records may associate predetermined ranges of fourth and fifth values D and E with particular injection device properties. This is represented graphically in FIG. 7. For example, if the location associated with a particular coloured surface portion 57 is determined to be in the area 70 then the injection device 10 having that surface portion 57 is determined to have a particular property. However, if the location associated with a particular coloured surface portion 57 is determined to be in the area 72 then the injection device 10 having that surface portion 57 is determined to have another property.

The shape of an area associated with a particular property, such as those denoted 70 and 72 in FIG. 7, may define any shape. For instance one or more of the areas 70, 72 in FIG. 7 could define a square, rectangle, polygon, circle or oval for instance. Consider the example in which an area defines a square that extends between 0.9 and 1.0 on both the vertical and horizontal axes in FIG. 7. In this example the combination of D=0.9 to 1.0 and E=0.9 to 1.0 is associated with short-acting insulin. If the respective fourth and fifth values D and E of a particular surface portion 57 are each determined to be within the range 0.9 to 1.0, then the injection device 10 having that surface portion is determined to contain short-acting insulin.

Further configuration of a supplemental device 34 is required such that different supplemental devices 34 determine substantially similar fourth and fifth values D and E for a surface portion 57 of the same colour. Graphically this means that further configuration is required such that different supplemental devices 34 determine surface portions 57 of the same colour to be associated with substantially similar locations in FIG. 7.

How such configuration is achieved will now be explained. A supplemental device 34 is configured such that if the surface portion 57 is a neutral colour (e.g. grey), the processor 40 determines the fourth and fifth values D and E to have predetermined magnitudes. The same occurs provided at least the part of the surface portion 57, from which light reflects onto the sensor 60, is neutral in colour.

The function f(A, B) used to determine the fourth value D may be such that the possible values of D range between 0 and 1. This function f(A, B) may also be such that if the surface portion 57 (specifically the part thereof from which light reflects onto the sensor 60) is a neutral colour (e.g. grey) the value of D is determined to be substantially 0.5.

A neutral coloured surface portion, for example a particular shade of grey, may have a reflectance of approximately 40% across all spectral ranges. In the foregoing example where the function f(A, B) comprises A/(A+B) the values of A and B will be substantially the same if the surface portion 57 is this colour. This is because (as already mentioned) the respective magnitudes of the first to third values A to C are proportional to a property of the first to third respective signals S1 to S3 that changes in accordance with the intensity of reflected light incident on the sensor 60 during a particular exposure time. Thus if the reflectance of the surface portion 57 is approximately 40% for light of the first to third wavelengths $\lambda_1$ to $\lambda_3$ then the respective values of A to C will be substantially similar. This provides that the fourth value D determined by calculating A/(A+B) will be substantially 0.5. Advantageously, if the function f(A, B) comprises A/(A+B) this minimises the effects of temperature drift imparted by the first light source 58a that emits light of the first wavelength for $\lambda_1$ for generating the first value A. This can be particularly useful where the first light source 58a is a red LED, because red LEDs are generally more susceptible to temperature drift than LEDs of colours such as blue and green.

The function f(C) used to determine the fifth value E may be such that the possible values of E also range between 0 and 1. For a neutral coloured surface having a reflectance of approximately 40% across all spectral ranges, the reflectance of light of the third wavelength $\lambda_3$ used to obtain the third value C will be 40% if the surface portion 57 (or at least the part thereof from which light reflects onto the sensor 60) is this colour. Such a colour may be the particular shade of grey mentioned in the previous paragraph. Calibration factors in the function f(C) may be set such that in this situation the value of E output from the function f(C) is substantially 0.4. These calibration factors are stored by the supplemental device 34, in the program memory 42 for example.

Consider a scenario in which a supplemental device 34 is calibrated in accordance with the previous two paragraphs. Such calibrated supplemental device 34, when coupled to an injection device 10 having a surface portion 57 that is of a shade of grey with a reflectance of approximately 40% across all spectral ranges, will determine the fourth and fifth values D and E to be those associated with the calibration location denoted 68 in FIG. 7.

In view of the foregoing it will be appreciated that in determining a property of an injection device 10 based on reflection characteristics of a surface portion 57, a supplemental device 34 could also utilise a three dimensional system which comprises two colour parameters D1 and D2 and one brightness parameter E. The two colour parameters D1 and D2 will be calculated as a function of (A, B, C). For example, D1=A/(A+B+C) and D2=B/(A+B+C). The brightness parameter E will be calculated similar to the foregoing as a function of C, E=f(C).

The heretofore described operation of the second optical sensor unit 56 is realised by the processor 40 operating in accordance with instructions contained in an operation application stored in the program memory 42. Relevant calibration information such as the calibrated exposure times (e.g. $t_1$ to $t_3$) and the aforementioned calibration factors may be accessed by the processor 40 operating in accordance with instructions contained in the operation application.

It will be appreciated that the above described embodiments are purely illustrative and are not limiting on the scope of the invention. Other variations and modifications will be apparent to persons skilled in the art upon reading the present application.

For example, in some embodiments the secondary optical sensor unit 56 comprises a plurality of different sensors 60 (for example, a plurality of photodiodes). However each such sensor is additionally provided with a filter configured to filter incident light such that only light of a particular wavelength (or range of wavelengths) is detected by the sensor. In such an embodiment the secondary optical sensor unit 56 comprises one or more sensors configured to detect reflected light of the first wavelength $\lambda_1$. The secondary optical sensor unit 56 also comprises one or more sensors configured to detect reflected light of the second wavelength $\lambda_2$. The secondary optical sensor unit 56 further comprises one or more sensors configured to detect light of the third wavelength $\lambda_3$. In this embodiment the processor 40 causes the first to third light sources 58a to 58c (or groups thereof) to concurrently emit light of the first to third wavelengths $\lambda_1$ to $\lambda_3$ onto the surface portion 57 in use. This provides that first to third signals similar to those heretofore described (i.e. first to third signals S1 to S3) are generated concurrently.

In the embodiment outlined in the previous paragraph, although the respective exposure times for light of different wavelengths elapse concurrently, such exposure times may be of different durations. This is for calibration purposes. Specifically, this is such that if a surface portion 57 (or at least the part thereof from which light reflects onto the sensors) is a neutral colour (e.g. grey), then the signals generated by the respective sensors in response to detecting light of the different wavelengths are substantially similar. More specifically in this situation the signals generated by the respective sensors, which are indicative of the intensity of reflected light of respective wavelengths during respective exposure times, are substantially similar.

Although it has been described that the reflection response of more than one wavelength of light is used to determine a property of an injection device, it is envisaged that in some other embodiments a property may be determined by analysing the reflection response of a single wavelength of light. Persons skilled in the art will be familiar with how data collected during such an analysis may be processed to make such a determination.

Finally, in some embodiments when the supplemental device 34 is in use light reflected from the surface portion 57 may be directed onto the sensor 60 via one or more reflective surfaces of the supplemental device 34 (e.g. mirrors). In such embodiments, although the surface portion 57 may be in the field of view of the sensor 60 in use, the surface portion 57 is not in the line of sight of the sensor 60.

Lastly, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A supplemental device comprising:
    a connector configured to attach the supplemental device to an injection device in use;
    a sensor configured to generate sensor output dependent on an intensity of light on the sensor and having a field of view directed at a surface area of the injection device in use, the surface area being external to the supplemental device;
    a plurality of light sources configured to generate illumination which in use is directed out of the supplemental device onto the surface area, wherein each light source of the plurality of light sources is configured to emit a different wavelength;
    a shield configured to limit the field of view of the sensor such that the field of view is entirely directed at the surface area in use;
    a memory storing a calibrated exposure time for each light source of the plurality of light sources, wherein the supplemental device is calibrated such that if the surface area is a neutral color then respective signals generated by the sensor, in response to detecting light of the different wavelengths, are substantially similar; and
    a processor configured to:
        for each light source of the plurality of light sources, illuminate the surface area with light for the respective calibrated exposure time; and
        use the sensor output generated when illumination from the plurality of light sources is reflected from the surface area to determine a property of the injection device, wherein using the sensor output generated when illumination from the plurality of light sources is reflected from the surface area to determine a property of the injection device comprises comparing the sensor output with one or more records, wherein each record associates a respective property of an injection device with a respective reflection response.

2. The supplemental device of claim 1, wherein a lens is not provided in the field of view of the sensor.

3. The supplemental device of claim 1, wherein a component with optical power is not provided in the field of view of the sensor.

4. The supplemental device of claim 1, wherein all transparent components in the field of view of the sensor have an optical power of zero.

5. The supplemental device of claim 1, wherein the shield is located between the plurality of light sources and the sensor.

6. The supplemental device of claim 1, wherein an aperture defined by the shield is located opposite the sensor, and wherein the aperture is configured to restrict or limit the field of view of the sensor.

7. The supplemental device of claim 6, wherein the aperture has a centre that is substantially aligned with a centre of the field of view of the sensor.

8. The supplemental device of claim 6, wherein the shield comprises a member that defines the aperture.

9. The supplemental device of claim 8, wherein the member is substantially frustum-shaped and the aperture is formed at the peak of the frustum.

10. The supplemental device of claim 6, wherein the aperture is defined by two side walls of the shield.

11. The supplemental device of claim 1, wherein the plurality of light sources comprise a plurality of LEDs that are arranged around the shield.

12. The supplemental device of claim 1, wherein the plurality of light sources comprise a plurality of LEDs that are arranged adjacent to one another substantially in a straight line.

13. The supplemental device of claim 11, wherein each of the LEDs in said plurality of LEDs is configured to emit a different wavelength of light.

14. The supplemental device of claim 11, wherein the processor is configured to cause each of the LEDs to emit light for the respective calibrated exposure times.

15. The supplemental device of claim 14, wherein the plurality of LEDS are controlled by the processor to sequentially emit light of the respective wavelengths.

16. The supplemental device of claim 1, wherein the supplemental device is configured for recording information about doses of medicament ejected from the injection device, in use.

17. The supplemental device of claim 1, wherein when the supplemental device is attached to an injection device in use, the supplemental device obstructs a dosage window of the injection device.

18. The supplemental device of claim 17, wherein the supplemental device further contains at least one optical sensor for gathering information indicative of what is displayed in the dosage window.

* * * * *